Nov. 4, 1975 G. N. NOBBIO Plant Pat. 3,799
PERPETUAL FLOWERING
CARNATION PLANT
Filed Nov. 19, 1974
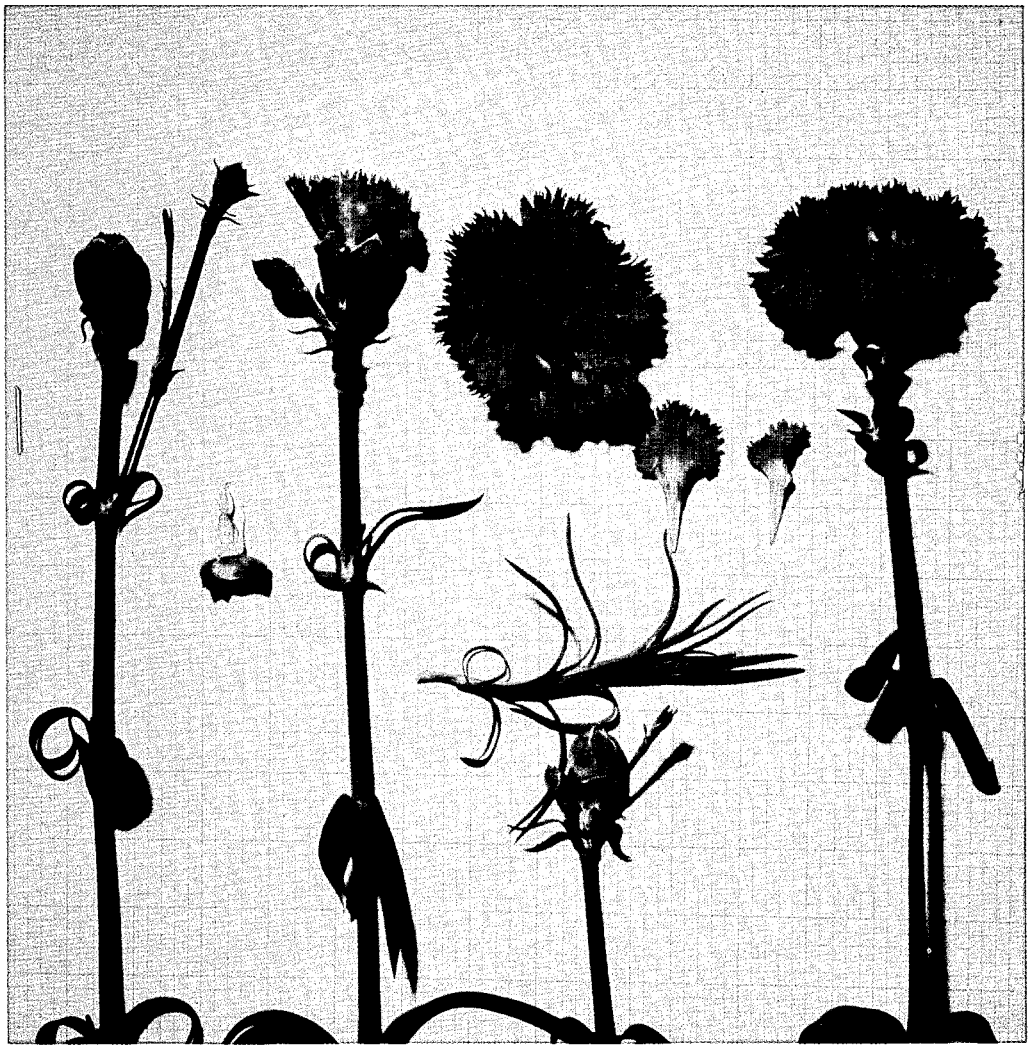

United States Patent

Plant Pat. 3,799
Patented Nov. 4, 1975

3,799

PERPETUAL FLOWERING CARNATION PLANT

Giacomo Nobbio, Duca degli Abruzzi 85, San Remo, Italy

Filed Nov. 19, 1974, Ser. No. 525,316
Claims priority, application Italy, May 17, 1974, 51,083/74
Int. Cl. A01h 5/00
U.S. Cl. Plt.—73 1 Claim

ABSTRACT OF THE DISCLOSURE

A variety of perpetual flowering carnation plant with slender growth and having flowers of a color between blood red and cardinal red.

BACKGROUND OF THE INVENTION

The present invention concerns a variety of perpetual flowering carnation plant, of the class having a generally closed calyx, that has been obtained by the applicant in the course of his study and research with a view to obtaining a new variety of carnation plant for the industrial production of cut flowers. He has sought to improve the qualities of the plant from both the point of view of cultivation and commerce on the international market.

In particular, by applying the laws of vetgetal genesis to the artificial fertilization of the flowers of various varieties of carnation, the present applicant sought to obtain a new variety of carnation having excellent vegetative qualities, very tall and slender growth, capable of providing very sturdy and rigid flower stems longer than the average stems of other varieties, and flowers of a particular shade of red much appreciated on the international cut flower market that would ensuret a degree of commercial success.

DESCRIPTION OF THE INVENTION

The variety of the present invention was obtained, after numerous unsuccessful attempts, by the artificial fertilization of flowers of the variety of carnation called "Davide," obtained by the same applicant, with pollen from an unpublished hybrid variety, classified under the number "6627," also obtained by the present applicant.

The new variety differs from the parent plants and from other varieties of its class. The result of the research may be considered as positive in that the new plant possesses, insofar as is possible, all the characteristics that were required. It constitutes a considerable improvement over the other varieties cultivated hitherto both in the ease with which it may be cultivated and in its high productivity of flowers for cutting.

The variety of the present invention may be reproduced easily and propagated in any number of specimens, all of them having the properties of the original plant, by means of one of the development methods of plant propagation normally used in flower cultivation. More particularly, this can be done by taking cuttings from one of the lateral buds, or from another part of the plant according to the present invention, or from plants derived from it by vegetative means, and then planting them in choice soil conditions until an adult plant, suitable for cut flower production, is obtained. By repeating the reproduction and propagation of the plant by this method, it has been ascertained that all the distinctive characteristics of the plant which is the subject of the present invention are transmitted in a constant and obsolutely faithful manner to all the specimens obtained so far, so that populations of plants with perfectly homogeneous and stable characteristics have been formed. Consequently, the present invention may be usefully employed on an industrial scale for the production of flowers for the cut flower market.

The properties which distinguish the present invention from other varieties of its class and permit its identification are given in the following description, accompanied by a photograph of the plant, by way of example alone and without any limitations. The description is based on a set of plants cultivated over a period of ten months on industrial lines both in the open air and in glass houses, in San Remo, Italy. The plants are described in the month of March.

Reference should always be made to these climatic and seasonal conditions in any comparison of this variety made as a function of the present description. Any possible differences which, as a result of different conditions of climate, soil or method of cultivation, may be encountered between certain features of the plant and the corresponding ones of the description must be considered normal and should not modify the essence of the present invention, at least so long as it is possible to identify the plant by means of the collection of features given in the description hereinbelow, by repeating the cultivation under the same conditions as those of the plants described.

In the description, the colors have been named according to the tables of the "Horticultural Color Chart" by Robert F. Wilson (indicated in the text by the initials HCC, followed by the page number and the shade) except in those cases in which the colors were absent from the tables or where its indication was sufficiently clear in common parlance.

Classification: Perpetual flowering hybrid carnation plant of the class having a generally closed calyx.

Stock: "Davide"—"unpublished hybrid number 6627."

PLANT

Growth: Very tall and vigorous plant, with dense and compact vegetation, thin and slender tuft. Numerous flower-bearing stems only slightly divergent from the axis of the plant, starting some distance above the soil.

Average height: 100–120 cm. from the soil level for fully developed plants cultivated as described above.

Roots: Very numerous, thin, ramified, starting in tufts from the collar, long, up to 150–200 mm., and 0.5–3 mm. in diameter at the collar, dig deep in soil. Long and thin root hairs. Color yellowish.

Main stem: Long, thin, slender, articulated in 2–3 elongated internodes, length varying from 50–60 mm., almost cylindrical in form, straight or slightly sinuous.

*Bark.*—Not very rough longitudinally.

*Color.*—Nut brown.

*Consistency.*—Almost woody, rigid, resistant.

*Average size.*—80–90 mm. in length from the collar to the first ramification, then a straight piece 100–150 mm. long on which the flower branches are inserted.

Flower branches: Numerous, on average 10–12 starting directly from the main stem or from the base of other flower branches, growing rapidly.

*Shape.*—Almost cylindrical, the diameter varying little from the base to the summit, thick, robust, erect, vertical, straight or slightly sinuous, articulated in internodes of varying length that increase slightly in diameter from the base to about the middle of the length, then decrease up to the flower.

*Average size.*—Length 90–100 cm. to the base of the flower, diameter 6–8 mm. at the base.

Internodes: Numerous, on average 18–20 on the flower branches.

*Shape.*—At the base short or of average length, almost cylindrical or fairly cylindrical in cross section, slightly enlarged toward the nodes. Middle higher internodes, length average to very long, almost cylindrical, slightly enlarged to massy toward the lower node, with longitudinal ribs and fasciations generally only slightly marked.

*Average size.*—Variable according to the stage of development and the position on the branch. Length increasing from the base to the internodes under the flower, as a general average: first internode from the base—15–20 mm.; second internode 15–20 mm.; third 15–20 mm.; fourth 25–30 mm.; fifth 25–30 mm.; sixth 25–30 mm.; seventh 25–30 mm.; eighth 30–35 mm.; ninth 30–35 mm.; tenth 35–40 mm.; eleventh 50–55 mm.; twelfth 50–55 mm.; thirteenth 50–55 mm.; fourteenth 60–65 mm; fifteenth 70–75 mm.; sixteenth 80–90 mm.; seventeenth 100–110 mm.; eighteenth 100–115 mm.; nineteenth 85–95 mm.; twentieth 50–55 mm.; length of floral peduncle 5–8 mm.

*Diameters.*—At the base 5–8 mm.; mid-stem 7–9 mm.; under the flower 3–5 mm.

*Color.*—Basic color Parsley Green (HCC, p. 193, shades 00962–00962/1) covered with lines of a waxy cuticle color Carnation Leaf Green (HCC, p. 194, shade 00058/1–2–3).

*Bark.*—Thick, smooth, hairless, opaque, pruinose in places.

*Consistency.*—Thick, almost woody, resistant.

Leaves: Abundant, sized average to large, inserted in opposing pairs on all the nodes, joined at the base by a foliar sheath which surrounds the node and the lower part of the internode above over an average height of 5–7 mm., generally whole, sometimes open on one side of the node.

*Shape.*—Lowest leaves—of average length and averagely narrow, triangular, ensiform, with smooth edges converging to an averagely sharp point. Lamina carinate in an averagely open V-shape with a marked longitudinal groove on the upper face of the leaves. Veins with longitudinal ribs on the lower face. Middle and upper leaves—slightly wider than the lower leaves, slightly lanceolate, slightly narrower at the base. Edges smooth, glossy, converging to a sharp point. Concave lamina in an open V-shape or almost flat on the upper face of the leaves, with raised edges toward the tip. Averagely raised longitudinal vein on the lower face.

*Average size.*—Lower leaves—length 100–120 mm.; width 10–12 mm.; middle and upper leaves—length 130–150 mm.; width 12–16 mm.

*Surface.*—Smooth, hairless, slightly granulous, opaque, pruinose.

*Color.*—Basic color Spinach Green (HCC, p. 197, shades 000858/1-2) covered with lines of a waxy cuticle color Carnation Leaf Green (HCC, p. 194, shades 000858/1–2–3).

*Consistency.*—Thick, rigid, fleshy.

*Bearing.*—Lower leaves straight or slightly sinuous, divergent from the stem at angles of 50–90°. Middle and upper leaves down-curved in an ample curve, with a tendency to curl into a circle or spiral toward the top of the stem.

Lateral shoots: Generally few in number, inserted one by one on the axil of one of the leaves, then more frequent toward the base of the plant, with a tendency to form flower branches. The middle and upper lateral shoots of the stem tend to form secondary flower branches which bear small flower buds inserted up to the base of the calyx, sometimes higher than the main flower.

*Shape.*—Composed of 5–6 pairs of opposed leaves, inserted on the axis of the shoot at somewhat lengthy intervals. Leaves rolled upon themselves or divergent from the axis of the shoot.

*Average size.*—Length at mid-stem: 150–200 mm.

FLOWER

Bearing: Main flower terminal on the branch, straight, accompanied by 4–6 secondary buds borne by lateral flower branches, inserted on the highest nodes of the stem, up to the base of the calyx, sometimes higher than the main flower.

Closed flower bud: Large, globular or almost cylindrical, with obtuse tip and base. Opening of the bud pointed. Tips of the sepals adhere to the petals, sometimes slightly detached.

*Average size.*—Length 30–32 mm., diameter 24–26 mm.

Calyx: Of the type generally closed, large in relation to the flower, bell-shaped funnel-shaped toward the top, with the tips of the sepals adhering to the petals when the corolla is open.

*Average size.*—Corolla open: length 30–35 mm., diameter 28–35 mm.

*Sepals.*—5–6 in number, generally 6, fused together in a conical tube, culminating in short, broad tips, silghtly differentiated, forming a bulge at their base, on average 6–10 mm. long and 16–18 mm. wide at the base. Edges smooth, slightly squamous.

*Color.*—Exterior: base color Pea Pod Green (HCC, p. 120, shades 061–061/1) tinted with Spinach Green (HCC, p. 187, shades 0960/2–3) on the upper part, with fine longitudinal lines of Pea Pod Green (HCC, p. 120, shades 061/1–2–3). Inner face: Verona Green (HCC, p. 89, shades 660/2–3).

*Surface.*—Outer side—smooth, hairless, slightly satiny. Inner side—smooth, hairless, waxy, satiny.

*Consistency.*—Leathery, thick, resistant.

Little calyx: Very large in relation to the calyx. Composed of 4 cordiform bracts, slightly squamose on the edges, placed in opposite pairs and imbricated around the base of the calyx up to about half its length.

*Average size.*—Outer bracts—length 18–25 mm.; width 14–16 mm.; inner bracts—length 18–22 mm.; width 20–22 mm.

*Color.*—Pea Pod Green (HCC, p. 120, shades 061/1–2) tinted with Spinach Green (HCC, p. 197, shades 000858/1–2–3) over almost the whole surface.

Open corolla: Very double, average to large, slightly bumpy and globular, with regular, round outline slightly scalloped, indented and lined. Guard petals very undulating, falling back slightly onto the calyx. Central petals erect, vertical, pressed close together, folded lengthwise or curly, free. Center of the flower full, averagely raised. Profile of the flower—rounded fan shape, above and around the calyx.

*Average size.*—Diameter, when fully open 80–100 mm.; length of the flower from the receptacle to the summit of the petals 55–60 mm.

*General color.*—Between Blood Red. (HCC, p. 166, shades 820–820/1) and Cardinal Red (HCC, p. 168, shades 822–822/1–2).

*Petals.*—Numerous, on average 50–60, apart from a few petalloid stamens in the center of the flower, free, placed around the ovary.

*Shape.*—Guard petals well developed with lamina of average size, rounded fan shape, wider than long, irregularly undulating along their length and often down-curved at the sides. Outer edge indented with long, fine notches, and a few light deeper cuts. Lateral edges smooth, often curled and with a few notches through intersection with close petals.

Inner petals—more reduced and irregular lamina than in the outer petals, rounded or elliptical, wider than long, sometimes narrow fan-shape, folded down their length or curly. Outer edge indented, with long and fine notches, almost slashed, the cuts concerning about half the lamina. Lateral edges smooth, regular, converging toward the claw which is long, thin, robust.

*Average sizes.*—Outer petals—lamina—length 25–28 mm., width 32–35 mm.; claw—length 28–32 mm., width 1–10 mm.; inner petals—lamina—length 20–22 mm.; width 26–30 mm.; claw—length 24–26 mm.; width 1–6 mm.

*Color.*—Upper face—close to Geranium lake (HCC, p. 20, shade 20–20/1) at the base and in the center of the petal, with tints of Cardinal Red (HCC, p. 168, shades 822–822/1) toward the outer edge, with tones of Blood Red (HCC, p. 166, shades 820–820/1) on the parts exposed to the light. Lower face—close to Orient Red (HCC, p. 165, shades 819–819/1) tinted with Blood Red (HCC, p. 166, shades 820–820/1) toward the outer edge.

Claw: White with slight greenish shades at the base and red toward the edges of the lamina.

*Surface.*—Upper face—smooth, hairless, slightly velvety; lower face—smooth, hairless, satiny.

*Consistency.*—Average thickness, averagely fleshy, resistant.

*Reproductive organs.*—Stamens: not very numerous, on average 8–10, placed around the ovary or on the edge of the petal claw. Erect filaments, or slightly twisted, length up to 30–35 mm., thin, white, washed with red on the tips.

*Anthers.*—Almost always absent or imperfectly developed, sometimes present, of average size.

*Ovary.*—Average to large, having a superior ovary, pear-shaped and averagely ribbed. Styles—come out of the tip of the ovary, on average 4–5, generally 4, short, tapering, fleshy, straight or slightly sinuous, divergent from each other, white, washed with red on the inner side. Stigmas—present on the inner surface of the styles.

Scent: Not very noticeable, sweet, spicy tones.

Resistance of flowers to inclemency of weather: Very good.

Resistance of flowers to transport: Very good.

Resistance of flowers once cut: Remarkable.

Resistance of plant to disease: Very good.

Reflowering ability: Abundant and continuous.

Hardiness of plant for industrial cultivation: Very good.

I claim:

1. A perpetual flowering carnation of the class having a generally closed calyx characterized in that the first plant of this variety was obtained by artificial fertilization of flowers of the variety called "Davide" with pollen from another unpublished hybrid variety with red flowers classified under the number "6627," said plant having the following unique combination of characteristics:

a. from the physical standpoint: a plant that grows to an average height of 100–120 cm. from the ground, tall and slender, with dense and compact vegetation, a thin and erect tuft, with numerous long, thick, sturdy, erect, rigid, straight or slightly sinuous flower branches; having abundant foliage of average size, fleshy and resistant; having elegant and most harmoniously shaped flowers, very double, with guard petals slightly falling back onto the calyx, giving the corolla a slightly globular appearance, with a large calyx of the closed type, and a very large little calyx compared with the calyx; having a regular, round corolla of a color between Blood Red and Cardinal Red, of a special tone;

b. from the physiological standpoint: a plant that is resistant to cryptogamic disease and inclemency of weather, is hardy for industrial production; that has abundant flowers and is productive in all seasons; suitable for cultivation in the open air or under glass; which has flowers that are resistant to inclemency of weather and to transport, suitable for export, which last well when cut, slightly or not at all scented; and the flowers and other parts of the plant being suitable for reproduction by agamic means.

No references cited.

ROBERT E. BAGWILL, Primary Examiner